(12) United States Patent
Nakagawa

(10) Patent No.: US 8,022,086 B2
(45) Date of Patent: Sep. 20, 2011

(54) THERAPEUTIC AGENT FOR GLOMERULAR DISEASE

(75) Inventor: Takashi Nakagawa, Hachioji (JP)

(73) Assignees: Kowa Co., Ltd., Nagoya-shi (JP); Nissan Chemical Industries, Ltd., Tokyo (JP)

(*) Notice: Subject to any disclaimer, the term of this patent is extended or adjusted under 35 U.S.C. 154(b) by 460 days.

(21) Appl. No.: 11/718,156

(22) PCT Filed: Oct. 25, 2005

(86) PCT No.: PCT/JP2005/019538
§ 371 (c)(1),
(2), (4) Date: Apr. 27, 2007

(87) PCT Pub. No.: WO2006/046528
PCT Pub. Date: May 4, 2006

(65) Prior Publication Data
US 2009/0156636 A1    Jun. 18, 2009

(30) Foreign Application Priority Data
Oct. 29, 2004  (JP) ................................ 2004-315896

(51) Int. Cl.
A61K 31/47  (2006.01)
A61K 31/41  (2006.01)

(52) U.S. Cl. ........................................ 514/311; 514/381

(58) Field of Classification Search .................. None
See application file for complete search history.

(56) References Cited

U.S. PATENT DOCUMENTS

| | | |
|---|---|---|
| 5,102,888 A | 4/1992 | Fujikawa et al. |
| 5,196,444 A | 3/1993 | Naka et al. |
| 5,856,336 A | 1/1999 | Fujikawa et al. |
| 5,872,130 A | 2/1999 | Fujikawa et al. |
| 6,589,547 B1* | 7/2003 | Igari et al. .................. 424/426 |
| 7,413,751 B2* | 8/2008 | Devane et al. ............... 424/473 |
| 7,449,182 B2* | 11/2008 | Cedarbaum et al. ......... 424/134.1 |
| 2003/0078190 A1* | 4/2003 | Weinberg ......................... 514/1 |
| 2004/0116468 A1 | 6/2004 | Nakagawa et al. |
| 2006/0257474 A1 | 11/2006 | Nakagawa et al. |

FOREIGN PATENT DOCUMENTS

| | | |
|---|---|---|
| EP | 1 386 608 A1 | 2/2004 |
| JP | 01279866 | 11/1989 |
| JP | 7-2667 | 1/1995 |
| JP | 2003-530342 | 10/2003 |
| WO | WO 02/085363 A1 | 10/2002 |
| WO | WO 03/066606 A1 | 8/2003 |
| WO | WO 2005/046677 A2 | 5/2005 |
| WO | WO 2005/046677 A3 | 5/2005 |

OTHER PUBLICATIONS

Nie et al., J UOEH, abstract, Jun. 1, 2004, 1;26(2):165-77.*
Nie et al., (JUOEH, Jun. 1, 2004, 1;26(2):165-77.*
Iturbe-Rodriguez, Bernardo et al., "AT-1 receptor blockade prevents proteinuria, renal failure, hyperlipidemia, and glomerulosclerosis in the Imai rat", Kidney International, vol. 66, No. 2, pp. 668-675, 2004.
U.S. Appl. No. 11/574,678, filed Mar. 5, 2007, Nakagawa.
Markus Lassila, et al., "Antiproteinuric Effect of RAS Blockade: New-Mechanisms", Antihypertensive Therapy: Renal Injury, vol. 6, No. 5, 2004, pp. 383-392.
Robert H. Weiss, et al., "TGF-β- and Angiotensin-II-Induced Mesangial Matrix Protein Secretion is Mediated by Protein Kinase C.", Nephrology Dialysis Transplantation, vol. 13, No. 11, pp. 2804-2813, (1998).
Extended Search Report issued Feb. 28, 2011, in European Patent Application No. 05805252.3-1216/1806137.

* cited by examiner

Primary Examiner — Phyllis G. Spivack
(74) Attorney, Agent, or Firm — Oblon, Spivak, McClelland, Maier & Neustadt, L.L.P.

(57) ABSTRACT

The present invention relates to a preventive and/or therapeutic agent for a glomerular disease containing, as active ingredients, pitavastatin or a salt thereof and candesartan cilexetil or a salt thereof. The agent of the present invention exhibits an excellent effect in the prevention and/or therapy of a glomerular disease.

3 Claims, 1 Drawing Sheet

CC: candesartan cilexetil

PV: pitavastatin calcium

THERAPEUTIC AGENT FOR GLOMERULAR DISEASE

TECHNICAL FIELD

The present invention relates to an agent for prevention and/or therapy of a glomerular disease (hereinafter the agent may be referred to as a "preventive and/or therapeutic agent for a glomerular disease").

BACKGROUND ART

Primary glomerular nephritis (i.e. a glomerular disease in which glomeruli of the kidneys are affected) is clinically classified into seven types; i.e. acute nephritis after infection with hemolytic streptococcus, crescentic glomerulonephritis (rapidly progressive nephritis), IgA nephropathy, membranous nephropathy, membranous proliferative nephritis, focal glomerulosclerosis and minimal change nephrotic syndrome. Generally, the diseases other than acute nephritis after infection with hemolytic streptococcus, crescentic glomerulonephritis and minimal change nephrotic syndrome are collectively called "chronic glomerular nephritis," and in many cases the cause and time of the onset of chronic glomerular nephritis are not well elucidated. In chronic glomerular nephritis the pathological process is generally progressive, and often results in renal failure or requirement for dialysis.

A drug which radically cures such a glomerular disease has not yet been developed, and thus a steroidal agent, an anti-platelet agent, an anticoagulant, an immunosuppressant or a similar drug has been employed for the purpose of pharmacotherapeutically suppressing or retarding the progression of the disease to the point of requiring dialysis. In recent years, a renin-angiotensin system inhibitor (e.g., an angiotensin II receptor blocker (ARB)) has been employed for such a purpose.

Among the aforementioned drugs, an ARB has been reported to exhibit the effect of suppressing an increase in systemic blood pressure through inhibition of angiotensin II (type 1) receptor. In addition, an ARB has been reported to exhibit, in the kidneys, for example, the effect of reversing the increase in intraglomerular pressure due to dilation of efferent glomerular arterioles, and the effect of suppressing proliferation of mesangial cells. Therefore, use of this drug has been considered to contribute toward suppressing progression or exacerbation of a glomerular disease (see Non-Patent Documents 1 and 2).

In renal diseases, the degree of worsening of hyperlipidemia has been reported to be statistically correlated with the degree of proteinuria or impaired renal function. Therefore, a therapeutic agent for hyperlipidemia (e.g., simvastatin) has been employed in the therapy of a renal disease for the purpose of removing hyperlipldemia, which is a factor exacerbating the disease.

However, when an ARB or a hyperlipidemia therapeutic agent is employed singly, the effect of the drug in the therapy of a renal disease is limited, and is not sufficient.

Non-Patent Document 1: Lassila M, et al. Antiproteinuric Effect of RAS Blockade: New Mechanisms. Curr Hypertens Rep. 6 (5): pp. 383-92, 2004

Non-Patent Document 2: Weiss R H, et al.: TGF-β- and angiotensin-II-induced mesangial matrix protein secretion is mediated by protein kinase C. Nephrol Dial Transplant. 13 (11): pp. 2804-13, 1998

DISCLOSURE OF THE INVENTION

Problems to be Solved by the Invention

An object of the present invention is to provide a drug exhibiting an excellent effect in the prevention and/or therapy of a glomerular disease.

Means for Solving the Problems

In view of the foregoing, the present inventors have conducted extensive studies, and as a result have found that when an ARB and a hyperlipidemia therapeutic agent are employed in combination, particularly when candesartan cilexetil or a salt thereof and pitavastatin or a salt thereof (i.e., HMG-CoA reductase inhibitor) are employed in combination, a remarkable renal disease therapeutic effect is attained, as compared with the case where these drugs are employed singly, and therefore, employing these drugs in combination is useful for the prevention and/or therapy of a glomerular disease.

Accordingly, the present invention provides a preventive and/or therapeutic agent for a glomerular disease, the agent containing pitavastatin or a salt thereof and candesartan cilexetil or a salt thereof.

The present invention also provides use of pitavastatin or a salt thereof and candesartan cilexetil or a salt thereof for producing a preventive and/or therapeutic agent for a glomerular disease.

The present invention also provides a method for prevention and/or therapy of a glomerular disease, the method comprising administering an effective amount of pitavastatin or a salt thereof and candesartan cilexetil or a salt thereof to a subject in need thereof.

EFFECTS OF THE INVENTION

The preventive and/or therapeutic agent for a glomerular disease of the present invention is useful for the prevention and/or therapy of a variety of glomerular diseases, including chronic glomerular nephritis (e.g., IgA nephropathy, focal glomerulosclerosis, membranous nephropathy, or membranous proliferative nephritis), and acute glomerular nephritis (e.g., acute nephritis or rapidly progressive glomerular nephritis).

BEST MODE FOR CARRYING OUT THE INVENTION

Figure 1:
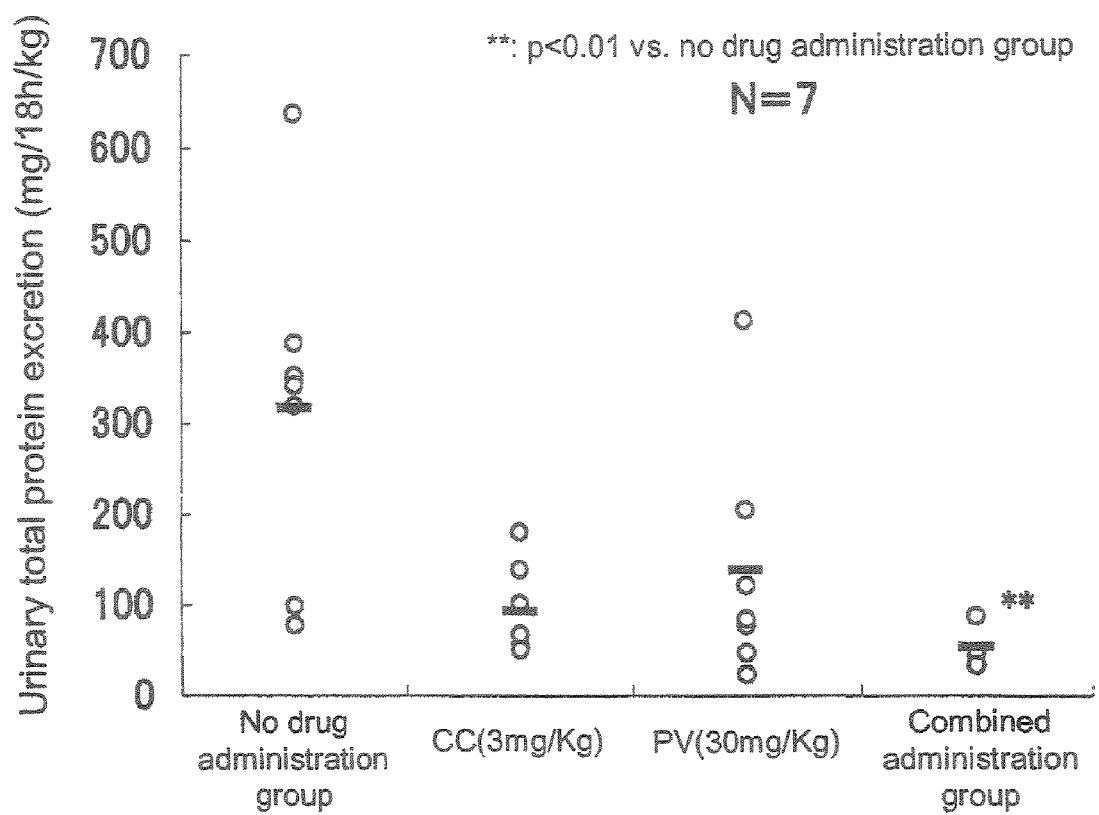
FIG. 1 shows urinary total protein excretion as measured after repeated oral administration of drugs for two weeks. The data points in FIG. 1 correspond to an individual value or an average value.

Pitavastatin ((3R, 5S, 6B)-7-[2-cyclopropyl-4-(4-fluorophenyl)-3-quinolyl]-3,5-dihydroxy-6-heptenoic acid), which is employed in the present invention, is known as an antihyperlipidemic agent exhibiting a potent HMG-CoA reductase inhibitory effect (Japanese Patent No. 2569746, U.S. Pat. No. 5,102,888, and European Patent No 304063). Pitavastatin is also known as a useful glomerular disease therapeutic agent (WO 02/85363).

Examples of pitavastatin species employed in the present invention include a free acid form, a salt thereof, and a lactone form. The salt form is preferably a sodium salt or a calcium salt.

Candesartan cilexetil (1-(cyclohexyloxycarbonyloxy) ethyl 2-ethoxy-1-[[2'-(1H-tetrazol-5-yl)biphenyl-4-yl]methyl]-1H-benzimidazole-7-carboxylate, which is employed in the present invention, is an angiotensin II receptor antagonist and is known to exhibit, for example, blood pressure lowering effect or heart failure ameliorating effect through such antagonizing action (JP-A-1992-364171 and U.S. Pat. No. 5,196,444). Examples of salts of candesartan cilexetil include a hydrochloride, a methanesulfonate, and a potassium salt.

The aforementioned pitavastatin or candesartan cilexetil can be produced through any of the methods disclosed in the aforementioned patent publications and Japanese laid-open patent applications, or through any known method.

The drug of the present invention employs pitavastatin or a salt thereof, and candesartan cilexetil or a salt thereof in combination. As described in the Example hereinbelow, administration of pitavastatin calcium and candesartan cilexetil in combination considerably reduces urinary total protein excretion in rat models of glomerular disease (i.e., rats are induced by rat glomerular basement membrane (rat GBM) antibody), as compared with the case of single administration of each of these drugs.

Therefore, the drug of the present invention is effective for the prevention and/or therapy of a glomerular disease in an animal, particularly for the prevention and/or therapy of a glomerular disease in a mammal including a human. Examples of such a glomerular disease include chronic glomerular nephritis (e.g., IgA nephropathy, focal glomerulosclerosis, membranous nephropathy, or membranous proliferative nephritis), and acute glomerular nephritis (e.g., acute nephritis or rapidly progressive glomerular nephritis).

In the preventive and/or therapeutic agent for a glomerular disease of the present invention, no particular limitation is imposed on the form of administration of pitavastatin or a salt thereof and candesartan cilexetil or a salt thereof. These drugs may be administered simultaneously, or each of the drugs may be administered separately at a certain interval. Alternatively, these drugs may be administered in the form of a combination drug.

Specifically, pitavastatin or a salt thereof and candesartan cilexetil or a salt thereof may be prepared into a single drug product by mixing these drugs with a pharmaceutically acceptable additive (e.g., a diluent or an excipient). Alternatively, the preventive and/or therapeutic agent may be prepared as a set (i.e., a kit) containing these drugs in separate drug products. In this case, these drug products may have product forms differ from each other.

The drug of the present invention can be prepared into pharmaceutical products of various forms in accordance with directions for use. Examples of the product forms include products for oral administration (e.g., a powder, a granule, a fine granule, a tablet, a capsule, and a dry syrup), and products for parenteral administration (e.g., an injection and a suppository).

Such a pharmaceutical product can be produced, in consideration of its product form, through a routine method by appropriately mixing with, diluting with, or dissolving in a pharmaceutically acceptable additive, such as an excipient, a disintegrant, a binder, a lubricant, a diluent, a buffer, an isotonizing agent, a preservative, a humectant, an emulsifier, a dispersant, a stabilizer, or a solubilizer.

For example, a powder product can be prepared by well admixing the active ingredients(s) (pitavastatin or a salt thereof and/or candesartan cilexetil or a salt thereof) with an appropriate optional additive such as an excipient or a lubricant. A tablet product can be prepared by mixing the active ingredient(s) with an appropriate optional additive such as an excipient, a disintegrant, a binder, or a lubricant, followed by tableting of the resultant mixture through a routine method. If necessary, the thus-obtained tablets may be subjected to coating to thereby yield film-coated tablets, sugar-coated tablets, etc.

An injection product may be in the form of a liquid formulation (aseptic aqueous or non-aqueous solution), an emulsion, or a suspension. Examples of non-aqueous carriers, diluents, solvents, and vehicles employed for preparing such an injection product include propylene glycol, polyethylene glycol, vegetable oils such as olive oil, and injectable organic acid esters such as ethyl oleate. The pharmaceutical composition may appropriately contain an auxiliary agent such as a preservative, a humectant, an emulsifier, or a dispersant.

In the drug of the present invention, the amount of pitavastatin or a salt thereof, or the amount of candesartan cilexetil or a salt thereof may be appropriately determined in consideration of the pharmaceutical product of the agent. For example, the amount of pitavastatin or a salt thereof is about 0.1 to about 10 mass %, preferably about 0.5 to about 5 mass %; whereas the amount of candesartan cilexetil or a salt thereof is about 1 to about 50 mass %, preferably about 10 to about 50 mass %.

In the present invention, as described above, a drug product containing pitavastatin or a salt thereof and a drug product containing candesartan cilexetil or a salt thereof may be administered simultaneously, or separately at a certain interval. In this case, the number of administration of the former drug product may differ from that of the latter one.

The dose of the agent of the present invention is appropriately determined in consideration of the body weight, age, or sex of a patient in need thereof, or the type or symptom of the glomerular disease of the patient. For example, the daily dose of pitavastatin or a salt thereof is 0.1 to 40 mg, preferably 1 to 20 mg, whereas the daily dose of candesartan cilexetil or a salt thereof is 0.1 to 100 mg, preferably 1 to 20 mg. Such a daily dose may be administered once a day, or in a divided manner (several times a day).

EXAMPLE

The present invention will next be described in more detail by way of an Example, which should not be construed as limiting the invention thereto.

Example 1

Pharmacological Test Employing Rat Model of Glomerular Basement Membrane (GBM) Nephritis Wistar male rats (six weeks old, purchased from Japan Laboratory Animals, Inc.) were quarantined and acclimatized for four days, and employed for the test. Firstly, a rat GBM rabbit IgG antibody was prepared, and then an antibody solution was adjusted with saline upon use to be 31 mg IgG antibody/mL saline. Thereafter, each of the rats was fixated under unanesthetized conditions, and the antibody solution was intravenously administered (1 mL/kg) through the tail vein, whereby progressive renal disorder was induced. The resultant rats were divided into four groups (N=7 for each), and immediately thereafter, the below-described test was carried out.

Specifically, the rats were divided into the following groups: group of administration of pitavastatin calcium (30 mg/kg) suspended in 0.5% aqueous methyl cellulose solution (N=7); group of administration of candesartan cilexetil (3 mg/kg) (N=7); group of administration of pitavastatin calcium (30 mg/kg) suspended in 0.5% aqueous methyl cellulose solution and candesartan cilexetil (3 mg/kg) in combination (N=7); and control group (i.e., no drug administration group) (N=7). In the drug administration groups, the respective drugs were repeatedly orally administered for two weeks.

In each of the groups, after completion of two-week drug administration, urine was collected from each rat for 18 hours in a metabolic cage (Product of Sugiyama-Gen Iriki Co., Ltd.), and urinary total protein excretion was measured. The results are shown in FIG. 1.

As shown in FIG. 1, in the no drug administration group (i.e., control group), 18-hour urinary total protein excretion was as high as 316 mg/18 h/kg. In the pitavastatin calcium administration group, 18-hour urinary total protein excretion was as low as 138 mg/18 h/kg, which was lower, but not significantly lower, than that in the case of the control group. In the candesartan cilexetil administration group, 18-hour urinary total protein excretion was as low as 92 mg/18 h/kg, which was lower, but not significantly lower, than that in the case of the control group.

In contrast, in the group of administration of pitavastatin calcium and candesartan cilexetil in combination, 18-hour urinary total protein excretion was very low; i.e., 54 mg/18 h/kg, which was significantly lower than that in the case of the control group (FIG. 1).

The invention claimed is:

1. A method for treating a glomerular disease comprising administering an effective amount of pitavastatin calcium and candesartan cilexetil to a subject in need thereof.

2. The method according to claim 1, wherein pitavastatin calcium and candesartan cilexetil are administered in a single drug product to a subject in need thereof.

3. The method according to claim 1, wherein pitavastatin calcium and candesartan cilexetil are separately administered in separate drug products to a subject in need thereof.

* * * * *